United States Patent [19]

Burgin

[11] Patent Number: 4,542,741
[45] Date of Patent: Sep. 24, 1985

[54] SURGICAL INSTRUMENT WITH INCORPORATED LIGHTING SYSTEM

[76] Inventor: Kermit H. Burgin, R.R. #1, Box 334, Whitestown, Ind. 46075

[21] Appl. No.: 552,323

[22] Filed: Nov. 16, 1983

Related U.S. Application Data

[63] Continuation of Ser. No. 284,506, Jul. 17, 1981, abandoned.

[51] Int. Cl.⁴ .............................................. A61B 17/32
[52] U.S. Cl. .................................. 128/303.1; 128/305; 362/119
[58] Field of Search ...................... 128/354, 305, 303.1, 128/13, 16, 18, 6; 30/123; 362/119

[56] References Cited

U.S. PATENT DOCUMENTS

| | | | |
|---|---|---|---|
| 2,226,616 | 12/1940 | Kraus | 362/119 |
| 2,247,258 | 6/1941 | Shepard | 128/16 |
| 2,588,288 | 3/1952 | Pohanka | 362/119 X |
| 2,822,615 | 2/1958 | Durst et al. | 362/119 X |
| 2,885,537 | 5/1959 | Wood | 128/16 |
| 3,093,135 | 6/1963 | Hirschhorn | 128/305 |
| 3,638,644 | 2/1972 | Reick | 128/16 |
| 4,053,979 | 10/1977 | Tuthill et al. | 128/305 X |
| 4,137,561 | 1/1979 | Andree | 362/119 |

FOREIGN PATENT DOCUMENTS

| | | | |
|---|---|---|---|
| 560135 | 4/1957 | Italy | 128/16 |
| 602084 | 7/1978 | Switzerland | 128/16 |
| 553728 | 6/1943 | United Kingdom | 128/6 |

Primary Examiner—Michael H. Thaler
Attorney, Agent, or Firm—Barnes & Thornburg

[57] ABSTRACT

A surgical instrument includes a blade, a handle supporting the blade, and a light source. The handle is constructed at least partially from a light-transmissive and optical waveguiding material and the light source directs light through the light-transmissive material to the blade to illuminate a field surrounding the blade to aid the surgeon using the instrument.

4 Claims, 7 Drawing Figures

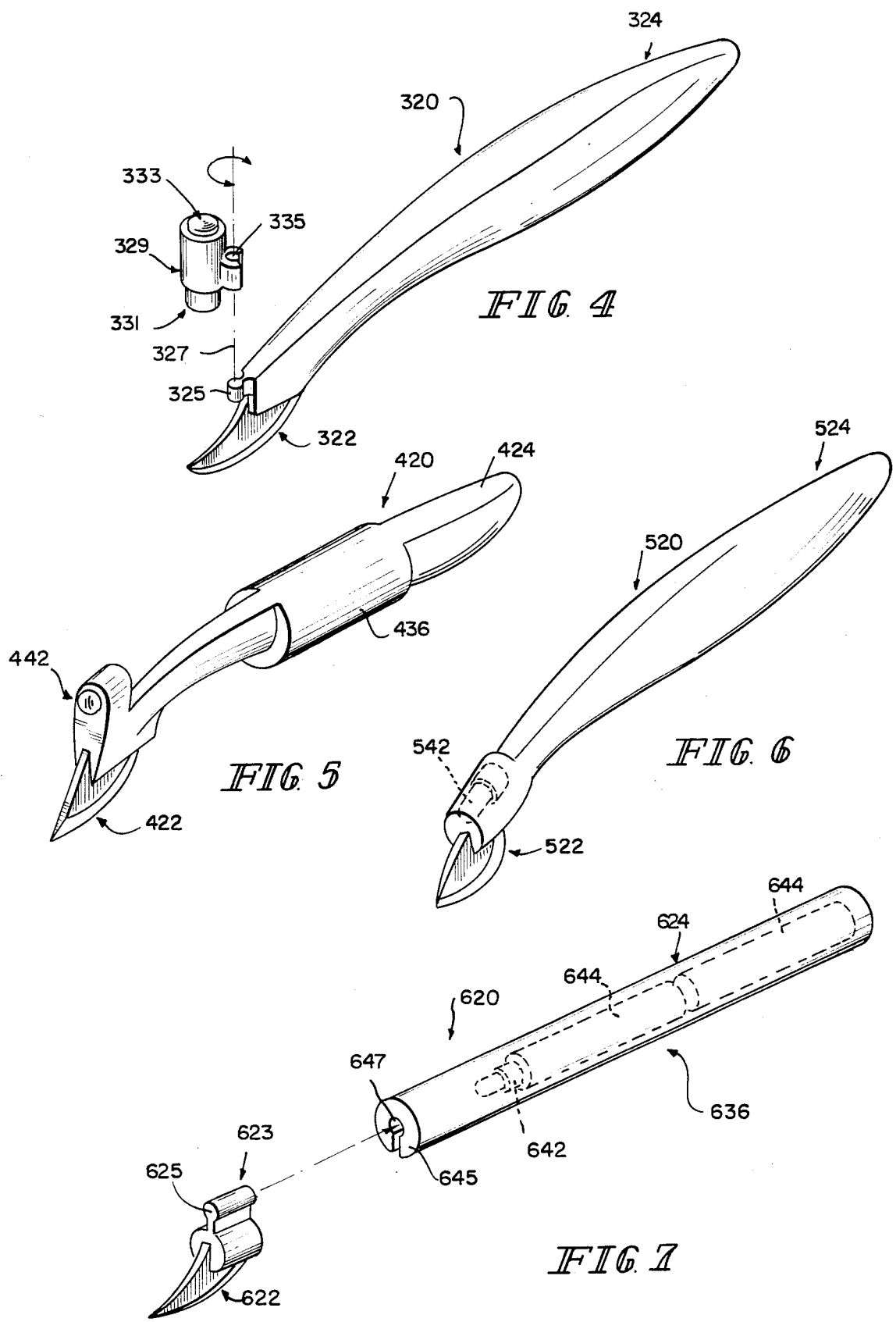

SURGICAL INSTRUMENT WITH INCORPORATED LIGHTING SYSTEM

This is a continuation of application Ser. No. 284,506 filed July 17, 1981, now abandoned.

This invention relates to surgical instruments, and particularly to an instrument in which the field upon which the instrument is to be used can be illuminated by the instrument.

A number of medical instruments utilizing fiber optic or acrylooptic characteristics are known. These include, by way of example, the devices described and illustrated in the following U.S. Pat. Nos.: 3,664,330; 3,762,400; 3,796,214; 3,716,047; 3,890,961; 2,247,258; 4,086,919; 3,851,642; 3,592,199; 3,324,850; 3,131,690; 2,482,971; 3,978,850; 2,690,745; 3,890,960; 3,916,881; 4,165,746; 4,263,899; and 4,156,424. There is also the device illustrated in German Offenlegungsschrift No. 2,302,614.

According to the invention, a surgical instrument includes a surgical instrument head, a handle supporting the head and a light source. The handle is constructed at least partially from a light-transmissive and optical waveguiding material and the light source directs light through the light-transmissive material to the surgical instrument head to illuminate a field where the instrument is to be used.

According to illustrative embodiments of the invention, means are provided on the handle adjacent the blade for directing light transmitted through the light-transmissive material toward the blade. Typically, the light-directing means can include means for providing a reflective surface on the handle and/or means for focusing or diffusing the light in the field to be illuminated.

Further according to the present invention, a surgical instrument includes an instrument head and a handle, a light source and means for coupling the light source to the handle to provide light to a field upon which the surgical instrument head is to be used.

Illustratively, the means for coupling the source to the handle includes a spine provided on one of the handle and source and an opening on the other of the handle and source, the opening have a cross section of a size and shape to engage the spine. Illustratively, the spine and opening have generally keyhole-shaped or generally circular cross sections.

Additionally according to the invention, a surgical instrument includes, in combination, an instrument head and a handle, one of the head and handle including means defining a spine and the other of the head and handle including means defining an opening, with the opening having a cross section of a size and shape to engage the spine.

Again, illustratively, the spine and opening have generally keyhole-shaped cross sections or generally circular cross sections.

Further according to this aspect of the invention, the combination includes a light source in the handle, and the blade includes a light-transmissive blade portion for transmitting light from the source to an area adjacent the blade to be illuminated.

The invention may best be understood by referring to the following description and accompanying drawings which illustrate the invention. In the drawings:

FIG. 4 is a partially exploded perspective view of another device constructed according to the present invention;

FIGS. 5–6 are perspective views of devices constructed according to the present invention; and FIG. 7 is a partly exploded perspective view of another device constructed according to the present invention.

Figure 1:
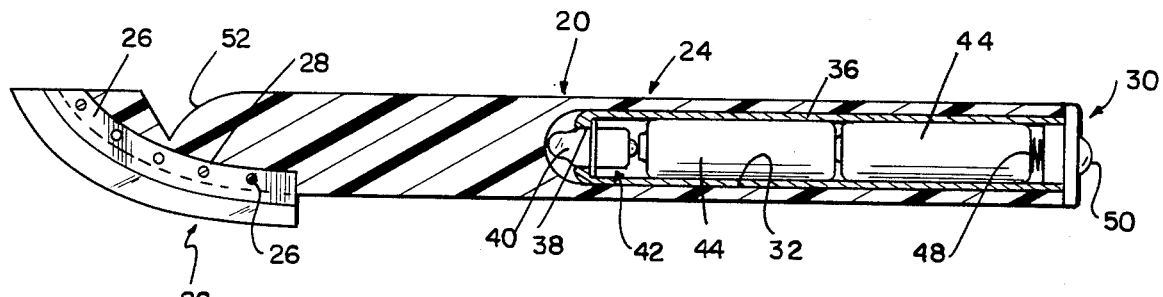
FIG. 1 is a longitudinal sectional view of a surgical instrument constructed according to the present invention.

With particular reference to FIG. 1, a surgical instrument 20 includes a surgical instrument head 22, here a scalpel blade, and a handle 24 which can be grasped by a physician to manipulate the blade 22. The handle 24 is typically molded from a polymethylmethacrylate-styrene mixture, and is highly transparent to transmit light. The blade 22 is molded into the handle 24 by means of holes 26 provided in the blade 22 adjacent its upper (non-working) edge 28. The material from which the handle 24 is molded flows through the holes 26 to secure the blade 22 to the handle 24.

The rearward end 30 of handle 24 is molded to provide a cavity 32. A metal cartridge 36 is press-fitted into cavity 32. Cartridge 36 has an opening 38 through its forward end through which the bulb 40 of a lamp 42 projects. Cartridge 36 is sufficiently large to accept two batteries, e.g., two "penlight" standard or alkaline cells 44. Cartridge 36 is closed by a spring 48-urged switch 50 so that lamp 42 is only energized when switch 50 is closed. Switch 50 illustratively is a latching type which, when closed, remains closed until depressed again to open.

A curved reflective surface 52 is molded into the forward end of handle 24 directly above blade 22. Surface 52 can be polished or otherwise treated (e.g., by plating with a composition which exhibits a mirror surface to the interior of handle 24). The surface 52 can be curved or contoured by molding in any desired shape or orientation to maximize the reflected light from source 42 downward to the field surrounding blade 22. The field can be fairly well illuminated by this system.

Figure 2:
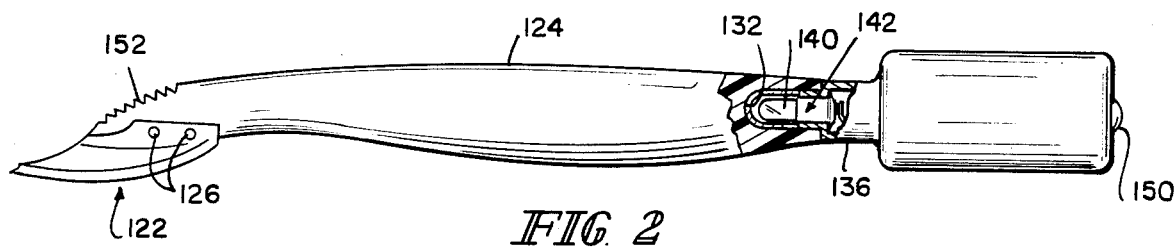
FIG. 2 is a partly fragmentary side elevational view of another device constructed according to the present invention.

Turning now to FIG. 2, another embodiment is illustrated. It includes a blade 122 molded through the use of openings 126 into a handle 124 which is contoured to fit the hand of a surgeon. A metal case 136 is molded onto the rearward end of handle 124. A lamp 142 having a bulb 140 projects into a cavity 132 provided at the rearward end of handle 124. Case 136 serves both as a battery case and as a mounting for a switch 150 which controls illumination of lamp 142. A serrated or sawtooth surface 152 is molded into the forward end of handle 124 above blade 122. Internal reflections of light from source 142 downward from surface 152 illuminate the field beneath blade 122. The surface 152 can be molded to the desired contour and finished, e.g., by polishing, plating or the like, to achieve the desired degree of reflection of transmitted light downward into the field.

Figure 3:
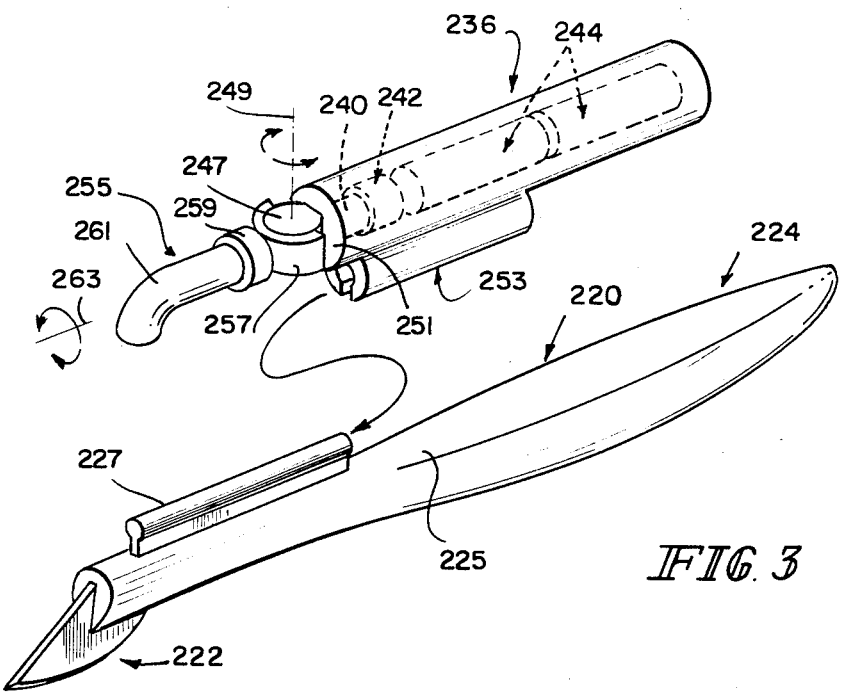
FIG. 3 is a partially exploded perspective view of another device constructed according to the present invention.

The device illustrated in FIG. 3 includes a blade 222 molded into a handle 224 which includes, along its upper surface 225 adjacent blade 222 a rib or spine 227. Spine 227 has a somewhat "keyhole-shaped" transverse section.

A separate battery pack and light source 236 houses penlight batteries 244, and a light source 242 including a bulb 240. The battery pack 236 illustratively is constructed largely from a highly transparent molded acrylic plastic (e.g., polymethylmethacrylate) and includes a generally cylindrical projection 247 having an axis 249 on its forward face 251. A somewhat keyhole-shaped opening which extends axially of battery pack 236 is molded into the bottom of the battery pack.

A light conductor 255, which is illustratively molded from acrylic plastic, includes a part-cylindrical resilient rearward member 257 which either slides axially of axis 249 onto projection 247 or snaps onto the projection. A collar 259 is molded onto member 257 and pivotally receives a light guide 261 which is pivotal about its own axis 263 to direct light from source 242 onto a portion of the field beneath blade 222. The battery pack 236 is slid onto the spine 227 for use with the instrument 220.

In FIG. 4, a surgical instrument 320 includes a blade 322 molded into a handle 324. The forward end of handle 324 directly above blade 322 includes a right circular cylindrical projection 325 having an axis 327. A battery pack 329 illuminates a light source 331 at the press of a switch 333. The battery pack 329 is mountable upon the projection 325 by means of the circular cross-section opening 335 molded into the battery pack 329. Battery pack 329 is rotatable about the axis 327 to illuminate a portion of the field beneath blade 322.

In the embodiment of the invention illustrated in FIG. 5, an instrument 420 includes a blade 422 molded into a handle 424 which includes a molded-in battery pack 436. Conductors (not shown) extend from the battery pack 436 forward to a light source 442 molded into handle 424 directly above the blade 422 and angled downwardly to illuminate a portion of the field around blade 422.

In the embodiment illustrated in FIG. 6, a battery case of the type illustrated in FIG. 1 (not shown in FIG. 6) is molded into the handle 524 of a surgical instrument 520. A blade 522 is also molded into handle 524 as is a light source 542 directly above blade 522. Conductors extend from the light source 542 rearwardly to the battery pack.

In the embodiment illustrated in FIG. 7, the blade 622 is molded into a blade assembly 623 which includes a keyhole-shaped cross-section rib or spine 625 on its upper surface. The molded acrylooptic handle 624 of instrument 620 includes a battery pack 636 which houses two penlight batteries 644 and a light source, lamp 642. Extending rearwardly from the front surface 645 of handle 624 toward lamp 642 is a keyhole-shaped cross-section opening 647 which is sized to engage the spine 625. The molded plastic portion of the blade assembly 623 is molded from an acrylooptic plastic, and light from source 642 is transferred through the assembly 623 and radiated upon the field around the blade 622.

In the embodiments of the invention illustrated in FIGS. 5-7, switches for energizing the lamps 442, 542, 642 were not shown for purposes of simplicity. It is to be understood, however, that such switches can be provided, and can be placed in orientations similar to switchs 50, 150 of FIGS. 1, 2, respectively, or can be placed such that by the act of grasping the handle 424, 524, 624 in FIGS. 5-7, respectively, the physician energizes the respective light source 442, 542, 642.

What is claimed is:

1. A surgical instrument comprising a handle having a long axis, an upper surface and a lower surface, a scalpel blade molded to the handle adjacent to the lower surface, the scalpel blade having a cutting edge, the handle supporting a light source, the handle constructed at least partially from a light-transmissive and optical waveguiding material, the light source being positioned to direct light through the light-transmissive material, and the handle including a smooth curved reflective surface, the curved reflective surface describing an arc generally in a plane generally parallel to the plane of the scalpel blade, the curved surface being provided on the upper surface of the handle at the forward end of the handle directly above the scalpel blade for directing substantially all of the light from the light source through the light-transmissive material and, with the aid of the curved reflective surface, onto the scalpel blade and the field surrounding the cutting edge of the scalpel blade.

2. A surgical instrument comprising a handle portion having a long axis, an upper surface and a lower surface, a scalpel blade having a cutting edge, the scalpel blade being molded into the handle portion adjacent to the lower surface, a battery case portion, and a light source, the scalpel blade being disposed at the forward portion of the handle, the battery case portion being disposed at the rearward portion of the handle and including a switch means for controlling the illumination of the light source, the light source being disposed adjacent the battery case portion, the handle portion being constructed at least partially from a light-transmissive and optical wave-guiding material and being contoured to fit the hand of a user, the light source and handle being configured to direct light in the handle generally along the long axis of the handle, the handle including a reflective portion provided in the upper surface at the forward end of the handle directly above the scalpel blade, the reflective portion being disposed in the light path to cause light to be reflected internally of the handle, to direct light transmitted in the handle portion along the light path downwardly through the light-transmissive material to illuminate the field directly beneath and around the cutting edge.

3. A surgical instrument comprising a handle portion, a scalpel blade molded to one end of the handle portion, a light source including a power source, a light bulb, and a light guide for directing light from the light bulb to a portion of the field beneath the blade, the light source including a forward face, a generally cylindrical projection having an axis which extends generally transverse to the longitudinal extent of the light source, the generally cylindrical projection provided on the forward face, a collar for pivotally engaging the light guide, a part-cylindrical resilient member molded to the collar, the resilient member pivotally engaging the generally cylindrical projection, and the forward face, the generally cylindrical projection, the resilient member, the collar, and the light guide all being constructed at least partially from light-transmissive material for directing light from the light bulb to a portion of the field beneath the blade, and means for selectively coupling the handle portion to the light source comprising a somewhat keyhole-shaped cross-section spine provided on the handle and a complementarily configured, somewhat keyhole-shaped cross-section passage on the light source, the opening having a cross section of a size and shape to engage the spine.

4. A surgical instrument comprising a handle portion having a long axis and a forward face, a scalpel blade molded to the handle portion, a light source means including a battery pack, a bulb, and a switch for controlling the illumination from the light source, and means for pivotally coupling the light source to the handle portion comprising a generally right circular cylindrical projection provided on the forward face of the handle portion, the cylindrical projection having an axis generally normal to the long axis of the handle portion, and a generally right circular cylindrical collar provided on the light source, the collar being selectively engageable with the projection to enable the light source to rotate about the axis of the projection.

* * * * *